United States Patent

Takeuchi

[19]

[11] Patent Number: 5,823,963
[45] Date of Patent: Oct. 20, 1998

[54] METHOD AND APPARATUS FOR STEREOSCOPIC ULTRASONIC IMAGING

[75] Inventor: Yasuhito Takeuchi, Tokyo, Japan

[73] Assignee: GE Yokogawa Medical Systems, Limited, Tokyo, Japan

[21] Appl. No.: 804,440

[22] Filed: Feb. 21, 1997

[30] Foreign Application Priority Data

Apr. 4, 1996 [JP] Japan .................................. 8-082467

[51] Int. Cl.$^6$ ........................................................ A61B 8/00
[52] U.S. Cl. ........................................... 600/443; 128/916
[58] Field of Search ..................... 928/660.07, 660.04, 928/660.09, 663.01, 661.01, 916; 600/440, 443, 445, 447; 128/916

[56] References Cited

U.S. PATENT DOCUMENTS

| | | |
|---|---|---|
| 3,895,525 | 7/1975 | Eichelberger . |
| 4,028,934 | 6/1977 | Sollish . |
| 4,652,086 | 3/1987 | Sandhu . |
| 5,379,769 | 1/1995 | Ito et al. ............................. 128/660.07 |
| 5,454,371 | 10/1995 | Fenster et al. . |
| 5,488,952 | 2/1996 | Schoolman .......................... 128/916 X |
| 5,503,152 | 4/1996 | Oakley . |
| 5,562,095 | 10/1996 | Downey et al. . |
| 5,617,225 | 4/1997 | Aritake et al. . |

FOREIGN PATENT DOCUMENTS

| | | |
|---|---|---|
| 0580353 | 1/1994 | European Pat. Off. . |
| 9600402 | 1/1996 | WIPO . |

*Primary Examiner*—Francis Jaworski
*Attorney, Agent, or Firm*—Moonray Kojima

[57] ABSTRACT

A stereoscopic ultrasonic imaging apparatus for displaying in a short time an ultrasonic image giving a sense of perspective. The apparatus comprises: two two-dimensional ultrasonic receiving element arrays arranged a predetermined distance apart; an orthoscopic image generation unit for generating a plurality of orthoscopic images of an observed surface perpendicularly intersecting an ultrasonic beam applied, the orthoscopic images having a predetermined parallax therebetween and generated on the basis of received ultrasonic data obtained by the element arrays; and a stereoscopic display unit for displaying stereoscopically the orthoscopic images generated by the orthoscopic image generation unit.

5 Claims, 8 Drawing Sheets

METHOD AND APPARATUS FOR STEREOSCOPIC ULTRASONIC IMAGING

BACKGROUND OF THE INVENTION

1. Field of the Invention

The present invention relates to a method and an apparatus for stereoscopic ultrasonic imaging and, more particularly, to a method and an apparatus for generating three-dimensional images through ultrasonic imaging at high speed.

2. Description of the Related Art

There exist methods for generating three-dimensional (3D) images through computer graphics. One such conventional method typically involves subjecting a plurality of ultrasonically acquired sectional views of an object to what is known as thresholding. More specifically, the thresholding extracts data on the desired object (i.e., target) from the multiple sectional views thereof, creates a rendering of the target such as a surface model (a 3D image composed of surfaces only) or a volumetric model (a 3D image depicting both surface and interior of the target) from the pixels of the extracted sectional view data, and generates and displays a definitive 3D image by shedding specifically directed light to the stereoscopic model thus rendered.

One disadvantage of the above conventional method is a large amount of time consumed in the process. Huge quantities of computations need to be carried out to deal with the relations between the pixels from the plurality of images (the process is intended to extract (i.e., generate) a new 3D image through calculations based on the volume image data made up of the plurality of sectional views). Illustratively, it takes at least one minute of processing to generate a 3D image from a plurality of typical ultrasonic images (sectional views).

Another disadvantage of the conventional method is the unpredictability of an eventually created 3D image varying with threshold settings. Little is known about what sort of 3D image will appear until it is actually generated by use of specifically designated threshold values. In determining the threshold settings for 3D imaging and display, it is mostly the operator's experience and intuitive knowledge that are resorted to.

SUMMARY OF THE INVENTION

It is therefore an object of the present invention to provide a stereoscopic ultrasonic imaging method for displaying in a short time an ultrasonically acquired image having a depth.

It is another object of the present invention to provide a stereoscopic ultrasonic imaging apparatus suitable for displaying in a short time an ultrasonically acquired image having a depth.

The invention, in short, envisages using at least two orthoscopic views to express a 3D image having a depth through stereoscopic imaging.

Throughout the description of this specification, a sectional view refers to a view of a target obtained on a Z-θ (or Z-X) plane in parallel with an ultrasonic beam, where Z denotes the direction of the ultrasonic beam viewed from a point of observation, and θ (or X) represents the direction in which the ultrasonic beam scans the target.

An orthoscopic view refers to a view of a target acquired on an X-Y plane perpendicularly intersecting an ultrasonic beam Z coming from a point of observation.

Stereoscopic imaging refers to an imaging method for representing two images acquired a predetermined basic line length apart, so that a sense of perspective is obtained from the parallax of the two images.

In specifically carrying out the invention and according to a first aspect thereof, there is provided a stereoscopic ultrasonic imaging method comprising the steps of: generating a plurality of orthoscopic images of an observed surface perpendicularly intersecting an ultrasonic beam, the plurality of orthoscopic images having a predetermined parallax therebetween; and displaying the plurality of orthoscopic images stereoscopically.

Preferably, at least two orthoscopic images having a suitable parallax therebetween should be prepared and displayed in such a manner as to form a stereoscopic image.

The inventive stereoscopic ultrasonic imaging method above causes a plurality of orthoscopic images of the observed surface perpendicularly intersecting the ultrasonic beam to be generated and displayed in stereoscopic form. This allows an observer to have a stereoscopic image of the observed surface.

In generating orthoscopic images for stereoscopic display of a target by the method, there is no need to perform conventional three-dimensional image processing in which a new 3D image is extracted through computations of volume image data formed by a plurality of sectional views of the target (the conventional process will be simply referred to as the computed 3D image processing hereunder). This means that the processing involved is completed in a very short time. A 3D vision derived from stereoscopic imaging allows the observer to have a sense of perspective in the orthoscopic images.

With the inventive method above, a number of orthoscopic images of a target may be created relative to at least two different visual points, and these images may be switched as desired when displayed. This makes it possible to realize a variety of stereoscopic visions of the target taken from different visual points.

According to a second aspect of the invention, there is provided a stereoscopic ultrasonic imaging apparatus comprising: orthoscopic image generation means for generating a plurality of orthoscopic images of an observed surface perpendicularly intersecting an ultrasonic beam, the plurality of orthoscopic images having a predetermined parallax therebetween; and stereoscopic display means for displaying stereoscopically the plurality of orthoscopic images generated by the orthoscopic image generation means.

Preferably, at least two orthoscopic images having a suitable parallax therebetween should be prepared and displayed by the above apparatus in such a manner as to form a stereoscopic image.

The inventive stereoscopic ultrasonic imaging apparatus above causes a plurality of orthoscopic images of the observed surface perpendicularly intersecting the ultrasonic beam to be generated and displayed in stereoscopic form. This allows an observer to have a stereoscopic image of the observed surface.

In generating orthoscopic images for stereoscopic display of a target with the apparatus, there is no need to perform the conventional computed 3D image processing. This means that the processing involved is completed in a very short time. A 3D vision derived from stereoscopic imaging allows the observer to have a sense of perspective in the orthoscopic images.

With the inventive apparatus, a number of orthoscopic images of a target may be created relative to at least two different visual points, and these images may be switched as desired when displayed. This makes it possible to realize a variety of stereoscopic visions of the target taken from different visual points.

In a first preferred structure of the stereoscopic ultrasonic imaging apparatus according to the invention, the orthoscopic image generation means generates a plurality of pairs of orthoscopic images relative to a plurality of visual points, each pair being made of two orthoscopic images; and the stereoscopic display means switches the visual points to display stereoscopically the orthoscopic images corresponding to the selected visual point.

In a second preferred structure according to the invention, any one of the inventive apparatuses above further comprises two two-dimensional ultrasonic receiving element arrays formed a predetermined basic line length apart, wherein the orthoscopic image generation means generates orthoscopic images based on received ultrasonic data from the two two-dimensional ultrasonic receiving element arrays.

With the second preferred structure, at least two orthoscopic images having a suitable parallax therebetween should preferably be prepared and displayed in such a manner as to form a stereoscopic image.

The inventive apparatus above uses the two-dimensional ultrasonic receiving element arrays to obtain orthoscopic images of the observed surface. This means that received ultrasonic data is obtained about the observed surface in a very short time.

Because two-dimensional orthoscopic images are generated for stereoscopic display by the apparatus, there is no need to perform the conventional computed 3D image processing. This means that the processing involved is completed in a very short time. A 3D vision derived from stereoscopic imaging allows the observer to have a sense of perspective in the orthoscopic images.

With the inventive apparatus in its second preferred structure, a number of orthoscopic images of a target may be created relative to at least two different visual points, and these images may be switched as desired when displayed. This makes it possible to realize a variety of stereoscopic visions of the target taken from different visual points.

In a third preferred structure according to the invention, any one of the preceding inventive apparatuses further comprises two one-dimensional ultrasonic receiving element arrays formed a predetermined basic line length apart and in parallel with each other, the element arrays being capable of scanning the ultrasonic beam in a basic line direction, wherein the orthoscopic image generation means generates orthoscopic images based on received ultrasonic data from the two one-dimensional ultrasonic receiving element arrays.

With the third preferred structure, at least two orthoscopic images having a suitable parallax therebetween should preferably be prepared and displayed in such a manner as to form a stereoscopic image.

In its third preferred structure, the inventive apparatus generates a plurality of orthoscopic images of the observed surface perpendicularly intersecting the ultrasonic beam and displays the generated images stereoscopically. This allows the observer to have a stereoscopic image of the observed surface.

With the preferred inventive apparatus, orthoscopic images of the observed surface are acquired by scanning with the two parallelly arranged one-dimensional ultrasonic receiving element arrays. This means that received ultrasonic data is obtained about the observed surface in a very short time.

Because two-dimensional orthoscopic images are generated for stereoscopic display by the apparatus, there is no need to perform the conventional computed 3D image processing. This means that the processing involved is completed in a very short time. A 3D vision derived from stereoscopic imaging allows the observer to have a sense of perspective in the orthoscopic images.

As with the preceding inventive apparatuses in their preferred structures, a number of orthoscopic images of a target may be created relative to at least two different visual points, and these images may be switched as desired when displayed. This makes it possible to realize a variety of stereoscopic visions of the target taken from different visual points.

Further objects and advantages of the present invention will be apparent from the following description of the preferred embodiments of the invention as illustrated in the accompanying drawings.

DESCRIPTION OF THE PREFERRED EMBODIMENTS

Preferred embodiments of the invention will now be described with reference to the accompanying drawings.

<Stereoscopic Ultrasonic Imaging Apparatus Embodying the Invention: First Apparatus Variation>

Figure 1:
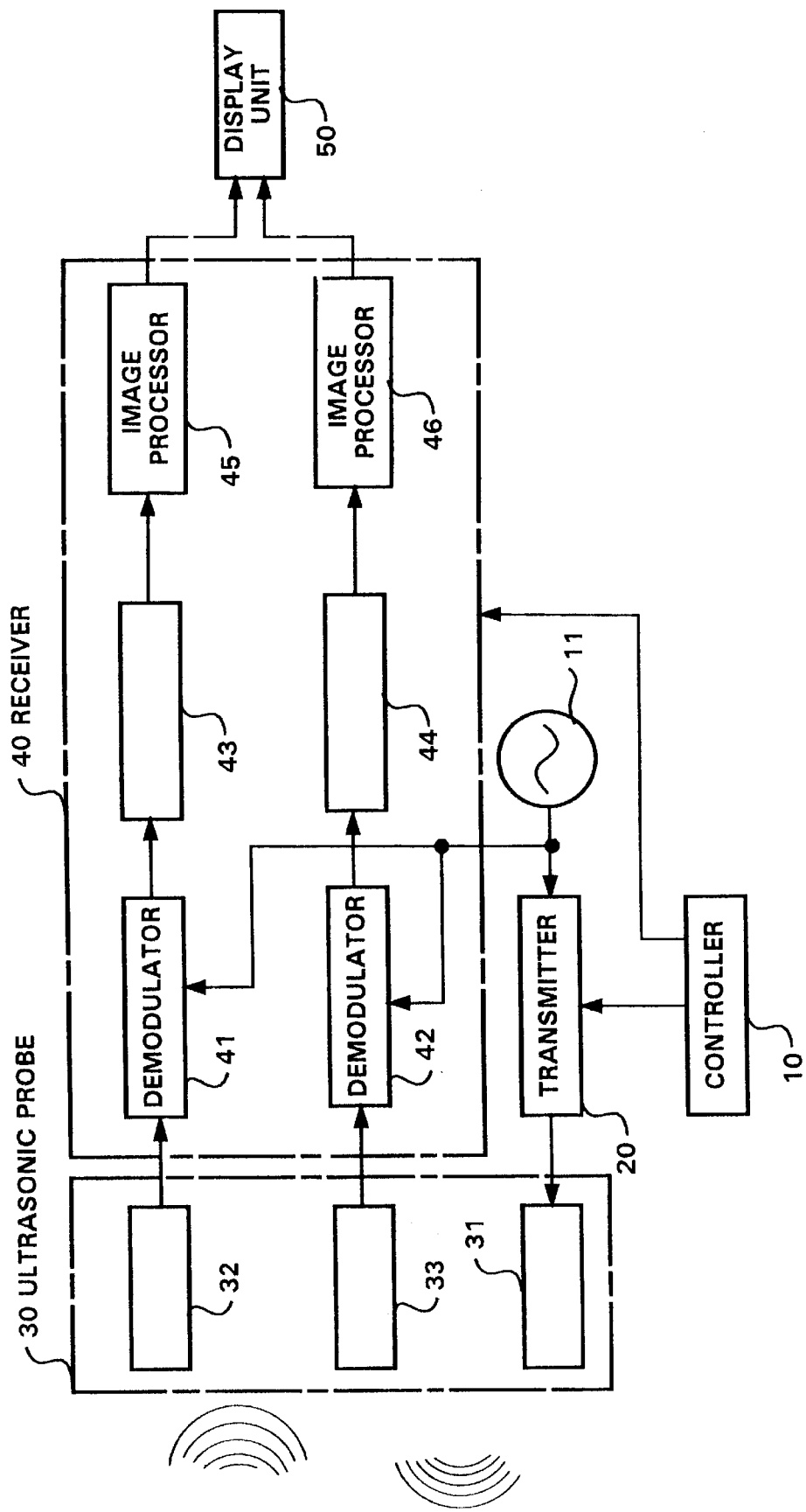
FIG. 1 is a block diagram of a stereoscopic ultrasonic imaging apparatus embodying the invention.

FIG. 1 is a block diagram of a stereoscopic ultrasonic imaging apparatus embodying the invention and acting as a basis for implementing a stereoscopic ultrasonic imaging method according to the invention.

An overall constitution of the apparatus is described first with reference to FIG. 1. In FIG. 1, reference numeral 10 denotes a controller that controls the apparatus as a whole, regulating ultrasonic transmission and reception as well as image processing.

An oscillator 11 is an oscillation means that generates a reference signal used in modulation and demodulation during ultrasonic transmission and reception. A transmitter 20 is a transmission means that generates a transmitted ultrasonic electrical signal upon receipt of the reference signal from the oscillator 11 under control of the controller 10.

An ultrasonic probe 30 is an electroacoustic transducer device which transforms the transmitted ultrasonic electrical signal into an ultrasonic beam to be sent to an object under observation and which converts back to electrical signals those ultrasonic signals that are returned from the observed object after being reflected thereby. The ultrasonic probe 30 is composed of a single ultrasonic transmitting element 31 and a plurality of ultrasonic receiving elements 32 and 33.

The ultrasonic transmitting element 31 is an electroacoustic transducer element that transforms into an ultrasonic beam the transmitted ultrasonic electrical signal coming from the transmitter 20. Positioned close to a target portion of the object under observation, the ultrasonic transmitting element 31 transmits an ultrasonic beam to the observed surface.

The ultrasonic receiving elements 32 and 33 are electroacoustic transducer elements arranged a predetermined distance apart (by a basic line length, to be described later). The elements receive the reflected ultrasonic signals from the observed object and convert the received signals into received ultrasonic electrical signals.

The ultrasonic receiving elements 32 and 33 are positioned close to the target portion of the observed object in order to receive ultrasonic signals reflected therefrom. The elements 32 and 33 are each constituted by a two-dimensional ultrasonic receiving element array on an X-Y plane or by a one-dimensional ultrasonic receiving element array formed in the X direction and scannable in the Y direction.

In the description that follows, the X-Y plane will signify an orthoscopic plane in the observed target (i.e., plane perpendicularly intersecting the transmitted ultrasonic beam). The X direction will refer to a depth of the observed target (i.e., direction along the transmitted ultrasonic beam).

A receiver 40 generates a stereoscopic image based on those orthoscopic images of the observed surface which are derived from two received ultrasonic electrical signals from the ultrasonic receiving elements 32 and 33. The receiver 40 comprises demodulators 41 and 42, two-dimensional FFT units 43 and 44, and image processors 45 and 46. The demodulators 41 and 42 demodulate the received ultrasonic electrical signals through quadrature detection or like processing. The two-dimensional FFT units 43 and 44 acquire two-dimensional images from the demodulated data through two-dimensional fast Fourier transformation (FFT). The image processors 45 and 46 generate display-ready image signals by subjecting the image data to suitable processes such as coordinate transformation and scanning frequency conversion.

A display unit 50 displays as a stereoscopic image the orthoscopic images generated by the receiver 40. The display unit 50 comprises various indicators and viewers capable of stereoscopic image indication.

Figure 2:
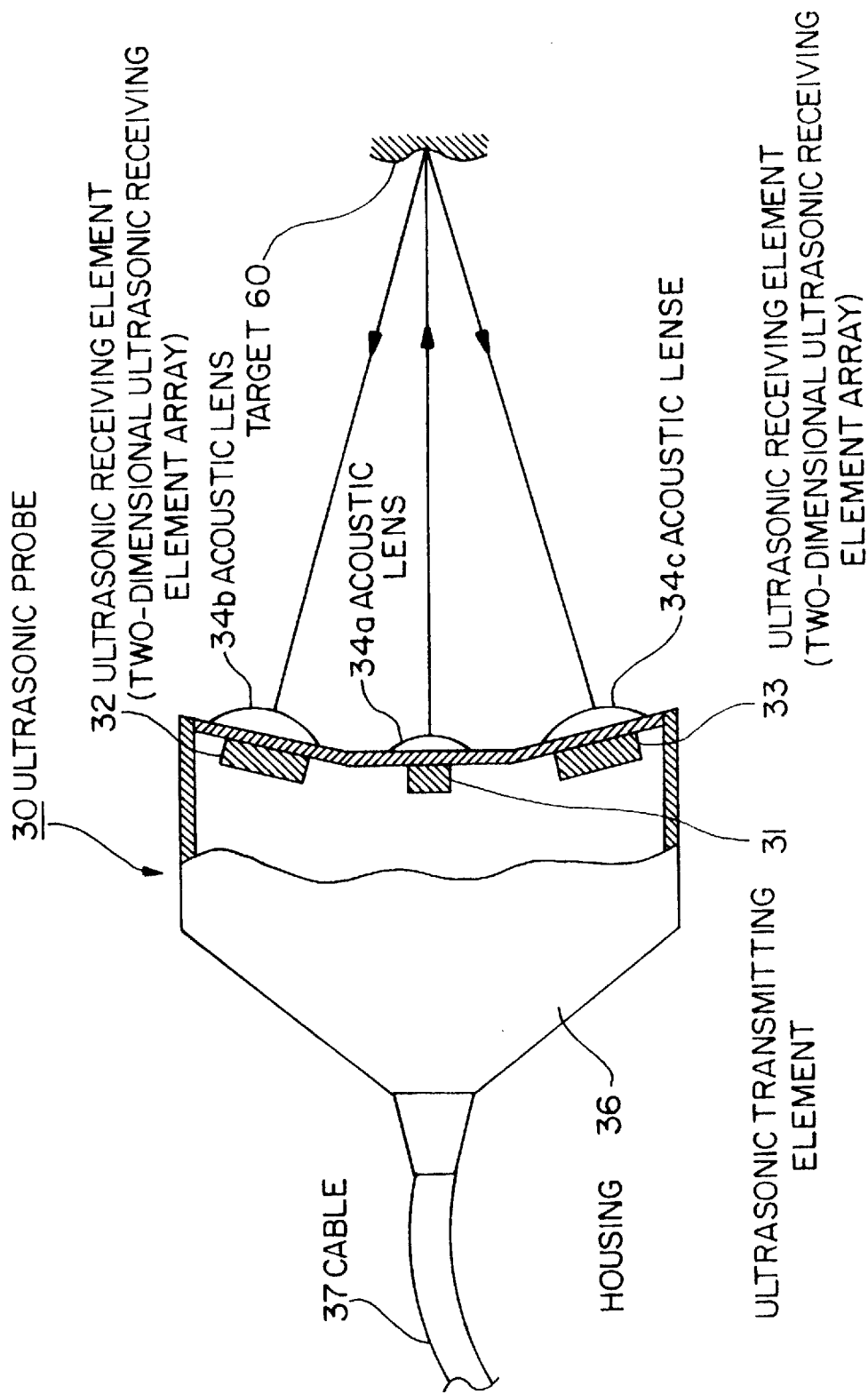
FIG. 2 is a partial sectional view of an ultrasonic probe acting as a key component of the embodiment in FIG. 1.

FIG. 2 is a partial sectional view of the ultrasonic probe 30. The view shows an typical setup utilizing two two-dimensional ultrasonic receiving element arrays.

In the example of FIG. 2, the ultrasonic transmitting element 31 is centrally located. The element 31 is flanked on both sides by the ultrasonic receiving elements 32 and 33 arranged a predetermined basic line length apart (i.e., relative distance between two points of view for stereoscopic observation). The basic line length should preferably be about the same as the distance between the eyes of the observer (about 6 cm).

The ultrasonic transmitting element 31 as well as the ultrasonic receiving elements 32 and 33 are furnished on their target-faced side with acoustic lenses 34a through 34c respectively. The lenses act to focus the transmitted and received ultrasonic beams. Preferably, the position where the ultrasonic beams to and from the acoustic lenses 34a through 34c converge should coincide, on the observed surface of a target 60, with the position where the center axis of the received ultrasonic beam for one ultrasonic receiving element 32 intersects the center axis of the received ultrasonic beam for the other ultrasonic receiving element 33. On the observed surface, the vicinity of the point of coincidence is most clearly viewed.

<Stereoscopic Ultrasonic Imaging Method Embodying the Invention: First Method Variation>

What follows is a description of how a stereoscopic ultrasonic imaging method embodying the invention is implemented in conjunction with the inventive stereoscopic ultrasonic imaging apparatus, and how the apparatus works.

Figure 3:
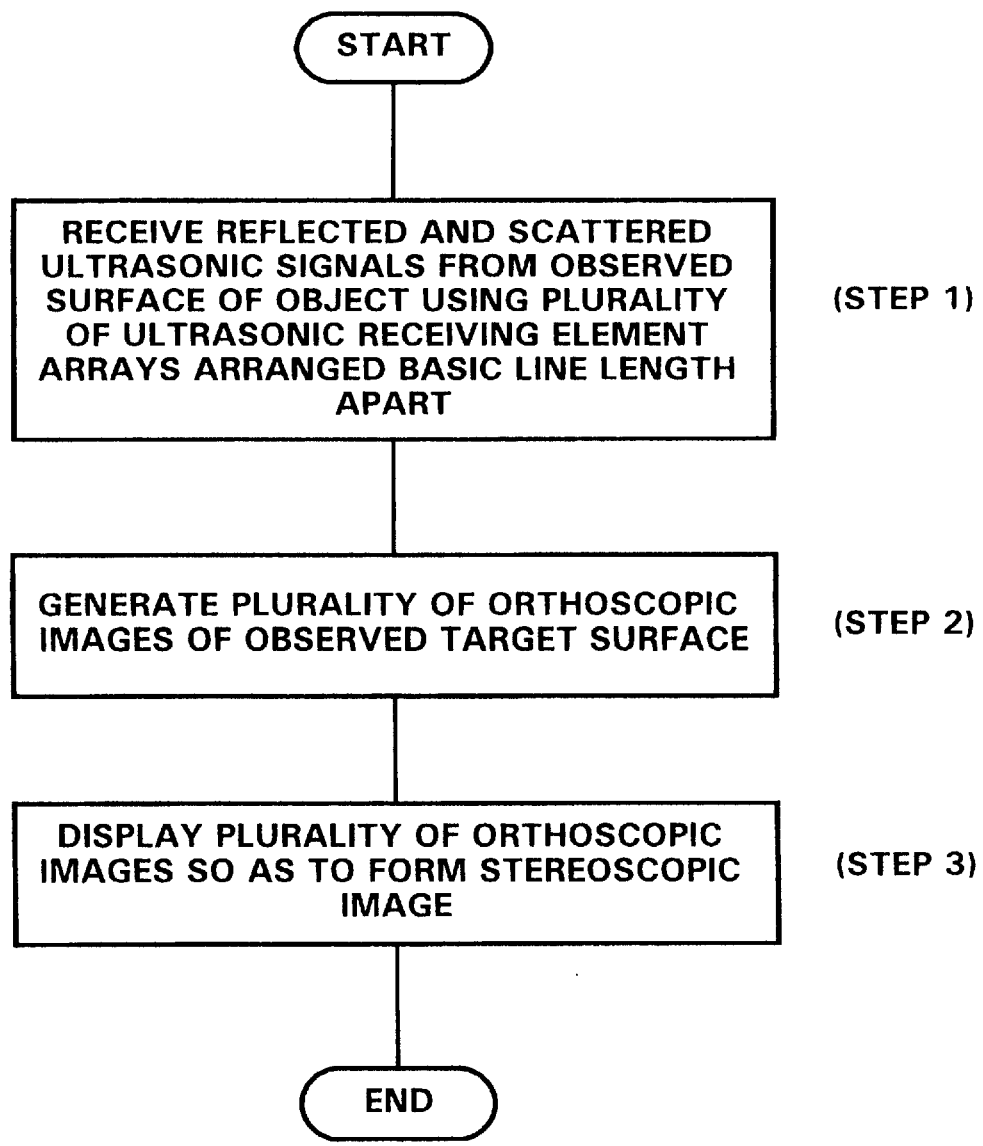
FIG. 3 is a flowchart of steps outlining a stereoscopic ultrasonic imaging method embodying the invention.

FIG. 3 is a flowchart of steps outlining how the stereoscopic ultrasonic imaging method according to the invention is executed in keeping with the workings of the inventive apparatus. The method is mainly composed of three steps. Each of these steps will now be described with reference to FIG. 3.

(1) Transmitting and receiving the ultrasonic beams (step 1 in FIG. 3)

A transmitted ultrasonic electrical signal generated by the transmitter 20 is sent to the ultrasonic transmitting element 31 in the ultrasonic probe 30. The element 31 converts the transmitted ultrasonic electrical signal into an ultrasonic signal and sends the converted signal to the target to be observed.

The transmitted ultrasonic signal reaching the target is reflected and scattered thereby. Part of the signal thus reflected and scattered returns to the ultrasonic probe 30 and converted to received ultrasonic electrical signals (also called received ultrasonic signals).

In this case, the separate positions of the ultrasonic receiving elements 32 and 33 give rise to apparent relative positional differences (i.e., parallax) of any object in the vicinity of the target 60. The received ultrasonic electrical signals thus reflect the parallax involved.

A conventional CW Doppler system is sufficient as an ultrasonic beam transmitting and receiving system for use with the invention. This is because the system need only generate orthoscopic images.

(2) Generating orthoscopic images (step 2 in FIG. 3)

The received ultrasonic electrical signals thus prepared by the ultrasonic probe 30 are demodulated by the demodulators 41 and 42. The demodulation is performed through quadrature detection or like processing with reference to the signal generated by the oscillator 11.

The demodulated data is fed to the two-dimensional FFT units 43 and 44. From the demodulated data, the FFT process generates orthoscopic image data about the observed surface perpendicularly intersecting the line of sight (i.e., ultrasonic beam).

The setup above comprises two two-dimensional ultrasonic element arrays as the ultrasonic receiving elements 32 and 33. This makes it possible to generate in a very short time two orthoscopic images (for orthography) and video signals associated therewith.

(3) Generating a stereoscopic image (step 3 in FIG. 3)

The image data generated by the two-dimensional FFT units 43 and 44 is supplied to the image processors 45 and 46. The image processors 45 and 46 subject the image data to necessary processes such as coordinate transformation and scanning frequency conversion, thereby generating video signals whose scanning frequency fits the display unit 50 for stereoscopic image display.

Given the video signals derived from the orthoscopic images and arranged for stereoscopic image display, the display unit 50 provides a stereoscopic image indication. In this case, any display devices or viewers capable of displaying stereoscopic images may be used.

Specifically, two orthoscopic images with a parallax therebetween are displayed the basic line length apart on a CRT display unit or an LCD unit. By watching the displayed images using a parallel viewing method or a cross viewing method, the observer acquires a sense of perspective based on the parallax.

While a single orthoscopic image is merely a two-dimensional image with no sense of depth (i.e., data in the ultrasonic beam (Z axis) direction), two orthoscopic images may be presented in a way that forms a stereoscopic image offering a sense of depth. This gives the observer a clear indication of distant and nearby objects in the field of the orthoscopic images being displayed.

An alternative setup for stereoscopic image display may involve the use of a fine lenticular lens arrangement behind which two orthoscopic images are divided and positioned alternately. Any one of other suitable stereoscopic image display methods may also be utilized.

The above processing as a whole provides both generation and display of two-dimensional image data. Even as orthoscopic images are being generated, necessary preparations for stereoscopic imaging can be initiated in real time. This makes it possible to carry out at a significantly high speed stereoscopic ultrasonic imaging and display.

<Benefits Available from the Above Embodiments: Part One>

The embodiments of the invention described above in detail offer the following major benefits:

(1) A plurality of orthoscopic images of the observed surface perpendicularly intersecting the ultrasonic beam applied are generated and displayed for stereoscopic display. By acquiring a stereoscopic image of the observed surface based on the orthoscopic images, the observer can get a clear picture of distant and nearby objects in the field of view.

(2) For stereoscopic imaging, the two-dimensional ultrasonic receiving element arrays are used to obtain orthoscopic images of the observed surface. This makes it possible to acquire in a very short time the received ultrasonic data about the observed surface.

(3) Because two orthoscopic images are generated for stereoscopic display, the process need only involve generating data about two two-dimensional images. With no need to carry out three-dimensional image processing through calculations, the generation of the data and the display thereof are completed very quickly in real time.

<Other Variations>

Figure 4:
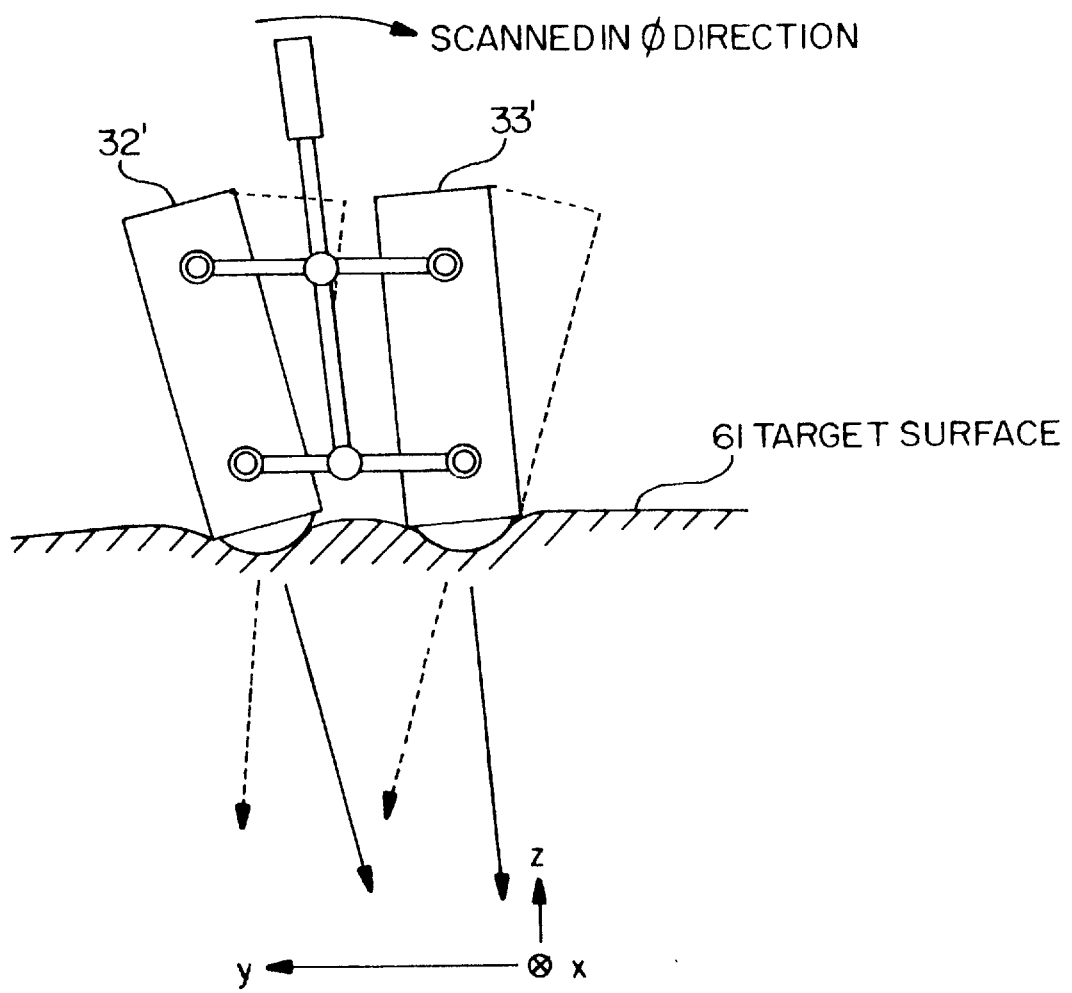
FIG. 4 is a schematic view of another type of ultrasonic probe used by the embodiment in FIG. 1.

In the above embodiments of the invention, the ultrasonic receiving elements 32 and 33 are made of two-dimensional ultrasonic receiving element arrays. Alternatively, the ultrasonic receiving elements 32 and 33 may be modified in the following manner:

As shown in FIG. 4, there may be provided ultrasonic receiving elements 32' and 33' each constituted by a one-dimensional ultrasonic receiving element array having a plurality of elements arranged perpendicularly (in the X direction) to the surface of the sheet of paper carrying the figure. The ultrasonic receiving faces of the elements 32' and 33' are arranged to be in parallel with an observed surface 61.

The ultrasonic receiving elements 32' and 33' are interlocked by a suitable mechanism that should allow the elements to be tiled together in a φ (Y) direction. Tilting of the elements in the φ direction may be accomplished either manually by the observer or mechanically.

Figure 5:
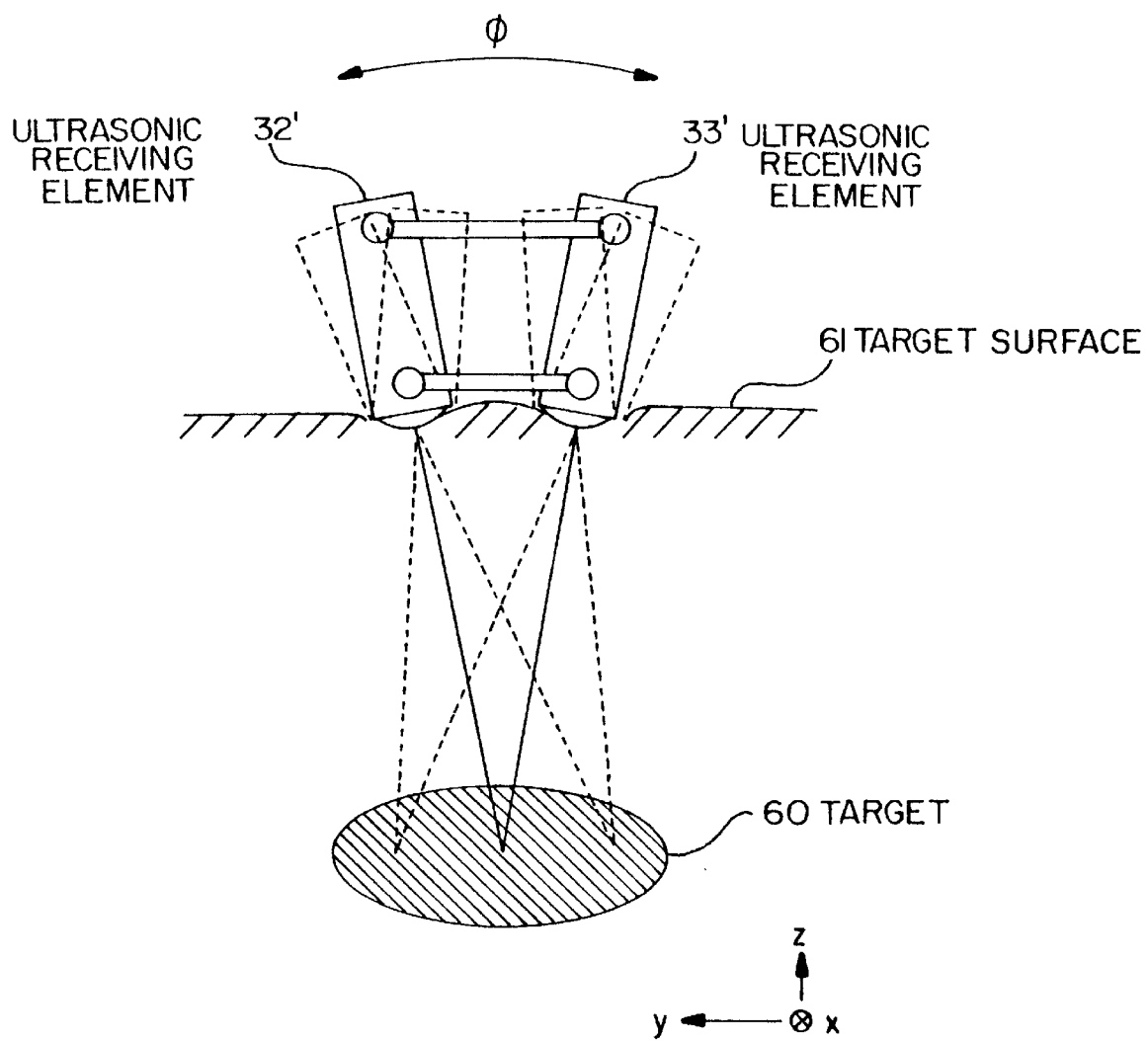
FIG. 5 is a a schematic view of another type of ultrasonic probe used by the embodiment in FIG. 1.

In the above setup, as illustrated in FIG. 5, the ultrasonic receiving elements 32' and 33' each made of a one-dimensional ultrasonic receiving element array in the X direction are scanned in the φ direction. The scanning operation yields two orthoscopic images having a parallax therebetween on the X-Y plane.

The two orthoscopic images thus obtained are displayed to form a stereoscopic image. Watching the stereoscopic image on display, the observer acquires a sense of perspective based on the parallax.

As described, a plurality of orthoscopic images are generated regarding the observed surface perpendicularly intersecting the ultrasonic beam applied. The orthoscopic images are displayed for stereoscopic imaging. Watching a stereoscopic image of the observed surface, the observer obtains a sense of perspective in the field of view.

In the case above, two one-dimensional ultrasonic receiving element arrays capable of scanning in an interlocked manner provide two orthoscopic images of the observed surface. This makes it possible to acquire in a very short time (e.g., upon completion of scanning) the received ultrasonic data about the observed surface.

Since the two orthoscopic images are used to generate a stereoscopic image, the process need only involve generating data about two two-dimensional images. With no need to perform three-dimensional image processing through calculations, the whole processing is completed very quickly.

<Stereoscopic Ultrasonic Imaging Apparatus Embodying the Invention: Second Apparatus Variation>

The stereoscopic ultrasonic imaging apparatus described with reference to FIGS. 1, 2, 4 and 5 has a pair of (i.e., two) ultrasonic receiving element arrays to generate a stereoscopic image. This means that the embodiment has the visual point determined by where the ultrasonic receiving element arrays are currently positioned.

When the above feature for visual point determination is extended, it is possible to implement another variation of the inventive apparatus comprising a plurality of ultrasonic receiving elements having a plurality of parallaxes therebetween. These elements are used to generate orthoscopic images that are switched so as to be viewed from one visual point after another.

Figure 6:
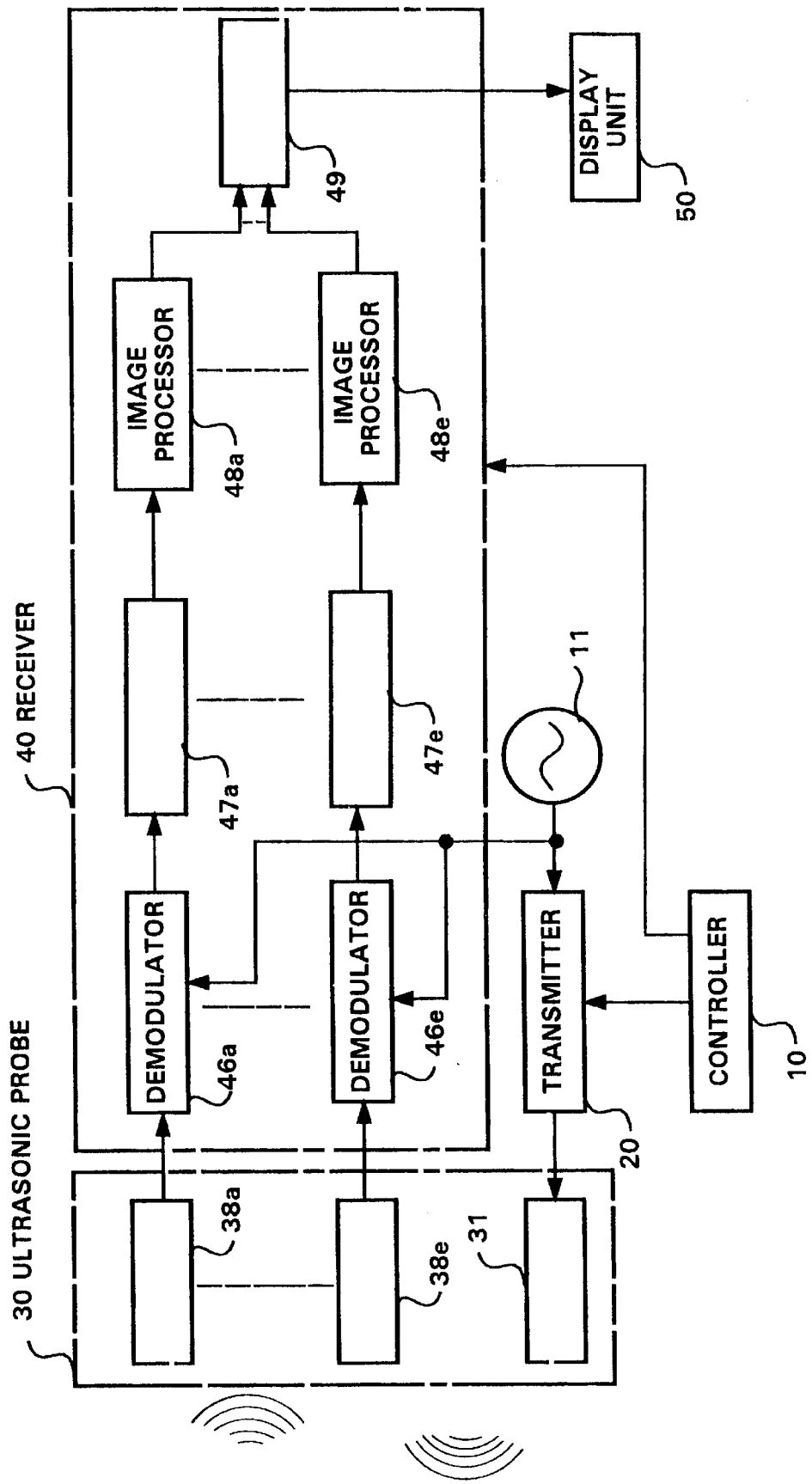
FIG. 6 is a block diagram of another stereoscopic ultrasonic imaging apparatus embodying the invention.

More specifically, a plurality of ultrasonic receiving elements 38a through 38e are furnished as shown in FIG. 6. The components of the receiver 40 (demodulators 46a through 46e, two-dimensional FFT units 47a through 47e, image processors 48a through 48e) are provided in numbers addressing the processing by the ultrasonic receiving elements configured. Each of the ultrasonic receiving elements generates an orthoscopic image.

A visual point changing unit 49 acting under control of the controller 10 selects orthoscopic images corresponding to a desired visual point. Whenever a new visual point is selected, the display unit 50 displays the orthoscopic images corresponding to the selected visual point. The visual points are switched as desired.

Figure 7:
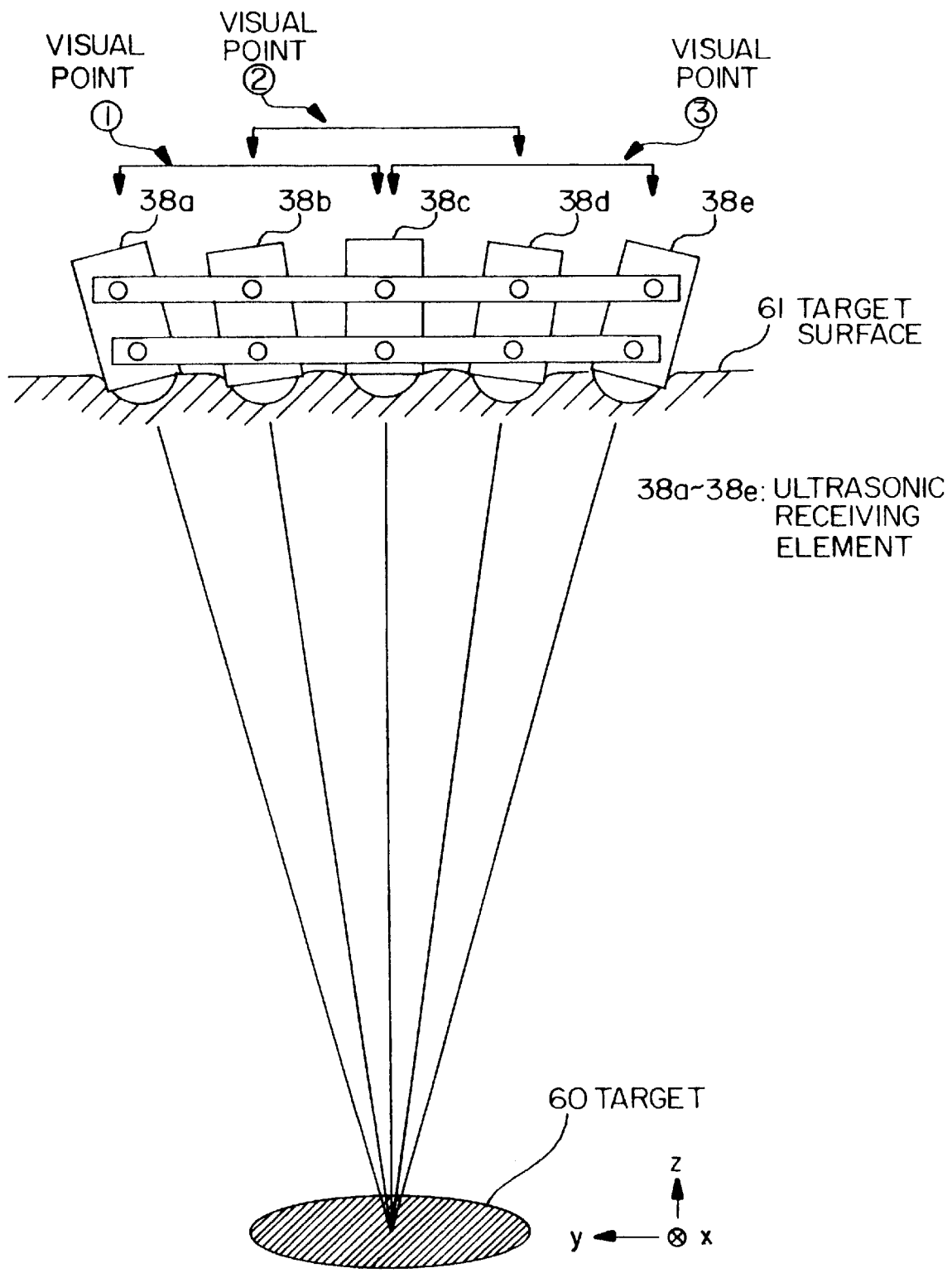
FIG. 7 is a schematic view of an ultrasonic probe acting as a key component of the embodiment in FIG. 6.

The ultrasonic probe 30 for use with the above setup may illustratively comprise one-dimensional ultrasonic receiving elements 38a through 38e formed in parallel with one another as shown in FIG. 7.

In the example of FIG. 7, the visual point is determined by the relationship between the distance between the ultrasonic receiving elements selected on the one hand, and the basic line length between the selected elements on the other hand. The position of the visual point is varied depending on how the ultrasonic receiving elements are selected with respect to one another.

In FIG. 7 the visual points are determined illustratively as follows:

Visual point (1): by ultrasonic receiving elements 38a–38c

Visual point (2): by ultrasonic receiving elements 38b–38d

Visual point (3): by ultrasonic receiving elements 38c–38e

The larger the number of ultrasonic receiving elements furnished, the finer the pitch by which the visual points are switched. While FIG. 6 shows a typical configuration involving a one-dimensional ultrasonic receiving element array, the visual point switching feature is also available with the setup of FIG. 2 involving the two-dimensional ultrasonic receiving element arrays. In the setup of FIG. 2, a plurality of pairs of ultrasonic receiving elements need only be provided to select any one of the multiple visual points successively.

<Stereoscopic Ultrasonic Imaging Method Embodying the Invention: Second Method Variation>

Figure 8:
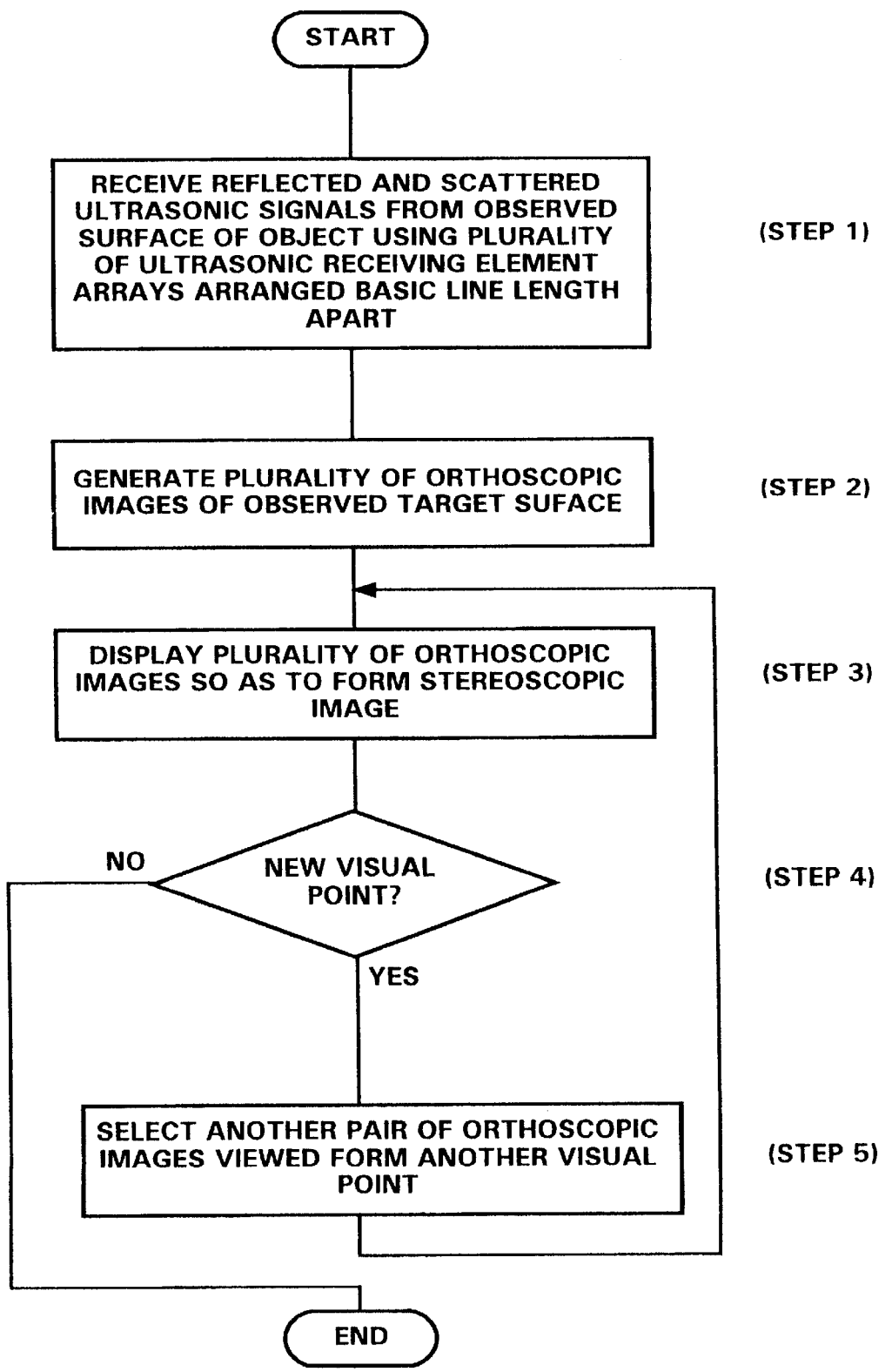
FIG. 8 is a flowchart of steps outlining another stereoscopic ultrasonic imaging method embodying the invention.

FIG. 8 is a flowchart of steps outlining how another stereoscopic ultrasonic imaging method embodying the invention is carried out in conjunction with the inventive stereoscopic ultrasonic imaging apparatus.

The method of FIG. 8 for stereoscopic ultrasonic imaging is mainly composed of four steps. Each of these steps will now be described with reference to FIG. 8.

(1) Transmitting and receiving the ultrasonic beams (step 1 in FIG. 8)

A transmitted ultrasonic electrical signal generated by the transmitter 20 is sent to the ultrasonic transmitting element 31 in the ultrasonic probe 30. The element 31 converts the transmitted ultrasonic electrical signal into an ultrasonic signal and sends the converted signal to the target to be observed.

The transmitted ultrasonic signal reaching the target is reflected and scattered thereby. Part of the signal thus reflected and scattered returns to the ultrasonic probe 30 and converted to received ultrasonic electrical signals (also called received ultrasonic signals).

In this case, the separate positions of the ultrasonic receiving elements 38a through 38e give rise to apparent relative positional differences (i.e., parallaxes) of any object in the vicinity of the target 60. The received ultrasonic electrical signals thus reflect the parallaxes involved.

(2) Generating orthoscopic images (step 2 in FIG. 8)

The received ultrasonic electrical signals thus prepared by the ultrasonic probe 30 are demodulated by the demodulators 46a through 46e. The demodulation is performed through quadrature detection or like processing with reference to the signal generated by the oscillator 11.

The demodulated data is fed to the two-dimensional FFT units 47a through 47e. From the demodulated data, the FFT process generates orthoscopic image data about the observed surface perpendicularly intersecting the line of sight (i.e., applied ultrasonic beam).

The setup above produces orthoscopic images (for orthography) of the observed surface representing the received ultrasonic data from each of the ultrasonic receiving elements 38a through 38e. This makes it possible to generate in a very short time the video signals denoting each of the orthoscopic images.

(3) Generating a stereoscopic image (step 3 in FIG. 8)

The image data generated by the two-dimensional FFT units 47a through 47e is supplied to the image processors 48a through 48e. The image processors 48a through 48e subject the image data to necessary processes such as coordinate transformation and scanning frequency conversion, thereby generating video signals whose scanning frequency fits the display unit 50 for stereoscopic image display.

Of the orthoscopic images thus generated, those whose video signals correspond to a first visual point are initially selected by the visual point changing unit 49. The selected video signals are displayed on the display unit 50 for a stereoscopic image indication.

Even as the orthoscopic images are being generated with respect to the first visual point, the stereoscopic image display process can be initiated at the same time. This makes it possible to carry out at a significantly high speed stereoscopic ultrasonic imaging and display.

(4) Changing the visual points (steps 4 and 5 in FIG. 8)

When the observer orders changing of visual points, the visual point changing unit 49 selects the video signal relative to another visual point and causes the display unit 50 to effect the corresponding display. There are two ways to select a new visual point for display: either the observer specifically designates a desired visual point, or the controller simply responds to a visual point change instruction by consecutively selecting one visual point after another.

Successively switching the visual points apparently causes a single visual point to change its position continuously. This makes it possible to have a stereoscopic image of the target as if the target were being rotated. The observer thus gets an even more precise sense of perspective in the field of view.

For stereoscopic imaging in the case above, any display devices or viewers capable of displaying stereoscopic images may be used. Illustratively, two orthoscopic images with a parallax therebetween are displayed the basic line length apart on a CRT display unit or an LCD unit. By watching the displayed images using a parallel viewing method or a cross viewing method, the observer acquires a sense of perspective based on the parallax.

While a single orthoscopic image is merely a two-dimensional image with no sense of depth (i.e., data in the ultrasonic beam (Z axis) direction), two orthoscopic images may be presented in a way that forms a stereoscopic image offering a sense of depth. This gives the observer a clear indication of distant and nearby objects in the field of the orthoscopic images being displayed.

<Benefits Available from the Above Embodiments: Part Two>

The variations of the invention described above in detail offer the following major benefits:

(1) A plurality of orthoscopic images of the observed surface perpendicularly intersecting the applied ultrasonic beam are generated and displayed for stereoscopic display. By acquiring a stereoscopic image of the observed surface based on the orthoscopic images, the observer can get a clear picture of distant and nearby objects in the field of view.

(2) For stereoscopic imaging, a plurality of two-dimensional ultrasonic receiving elements are used to obtain orthoscopic images of the observed surface. This makes it possible to acquire in a very short time the received ultrasonic data about the observed surface.

(3) Because a plurality of orthoscopic images are generated for stereoscopic display, the process need only involve generating two-dimensional image data. With no need to carry out three-dimensional image processing through calculations (i.e., generation of three-dimensional images from numerous two-dimensional cross-sectional images), the generation of the data and the display thereof are completed very quickly in real time.

(4) Stereoscopic images may be switched consecutively with respect to each of a plurality of visual points. This makes it possible for the observer to have an even more precise sense of perspective about the target as viewed from each of the successively and slightly different visual points. In this case, too, there is no need to perform three-dimensional imaging. With only two-dimensional image data to be generated, the whole process is completed in a very short time.

Many widely different embodiments of the invention may be constructed without departing from the spirit and scope of the present invention. It should be understood that the present invention is not limited to the specific embodiments described in the specification, except as defined in the appended claims.

What is claimed is:

1. A stereoscopic ultrasonic imaging method comprising the steps of:

applying an ultrasonic beam from at least one ultrasonic transmitting element to a three dimensional surface;

receiving in at least a pair of ultrasonic receiving elements separated from each other by a basic line length a pair of reflected ultrasonic beams and scattered light reflected by said three dimensional surface;

processing the reflected ultrasonic beams and scattered light received by the at least pair of ultrasonic receiving elements so as to form a pair of orthoscopic images having a predetermined parallax therebetween; and displaying the pair of orthoscopic images obtained by the processing in a stereoscopic manner so that a three dimensional image of the three dimensional surface is formed at high speed and without requirement of high volume calculations.

2. A stereoscopic ultrasonic imaging apparatus comprising:

transmitting means for applying an ultrasonic beam against a three dimensional surface;

receiving means, comprising at least a pair of ultrasonic receiving elements located a basic line length apart from each other, for receiving at least a pair of reflected ultrasonic beams and scattered light reflected from said three dimensional surface;

processing means for taking the at least pair of reflected ultrasonic beams and scattered light from the at least pair of ultrasonic receiving elements and processing the at least pair of reflected light beams and scattered light to form a pair of orthoscopic images thereof having a predetermined parallax therebetween; and display means for displaying the pair of orthoscopic images in a stereoscopic manner whereby a three dimensional image is obtained of said three dimensional surface with high speed and without requirement of high volume calculation of sectional views.

3. The apparatus of claim 2, wherein a plurality of pairs of orthoscopic images are obtained relative to a plurality of visual points, each pair being made of two orthoscopic images; and wherein said display means comprises means for switching said visual points to display stereoscopically the orthoscopic images corresponding to a selected one of said plurality of visual points.

4. The apparatus of claim 2 or 3, wherein said receiving means comprises two two-dimensional ultrasonic receiving element arrays formed in a predetermined basic line length apart from each other and connected to said processing means; and wherein said processing means generates said plurality of orthoscopic images based on ultrasonic beams and scattered light received from said two two-dimensional ultrasonic receiving element arrays.

5. The apparatus of claims 2 or 3, wherein said receiving means comprises two one-dimensional ultrasonic receiving element arrays formed in a predetermined basic line length apart from each other and in parallel with each other and connected to said processing means, said element arrays being capable of scanning the ultrasonic beams in a basic line direction, and wherein said processing means generates said at least pair of or plurality of pairs of orthoscopic images based on ultrasonic beams and scattered ligt received from said two one-dimensional ultrasonic receiving element arrays.

* * * * *